United States Patent
Habecker (12)

(10) Patent No.: US 11,911,297 B2
(45) Date of Patent: Feb. 27, 2024

(54) FOOT PROSTHESIS WITH DYNAMIC VARIABLE KEEL RESISTANCE

(71) Applicant: Matthew J. Habecker, Zionsville, IN (US)

(72) Inventor: Matthew J. Habecker, Zionsville, IN (US)

(*) Notice: Subject to any disclaimer, the term of this patent is extended or adjusted under 35 U.S.C. 154(b) by 209 days.

(21) Appl. No.: 17/136,369

(22) Filed: Dec. 29, 2020

(65) Prior Publication Data

US 2021/0113355 A1 Apr. 22, 2021

Related U.S. Application Data

(63) Continuation of application No. 15/916,520, filed on Mar. 9, 2018, now Pat. No. 10,874,528.

(Continued)

(51) Int. Cl.
*A61F 2/66* (2006.01)
*A61F 2/70* (2006.01)
(Continued)

(52) U.S. Cl.
CPC ............. *A61F 2/66* (2013.01); *A61F 2/6607* (2013.01); *A61F 2/70* (2013.01); *A61F 2/60* (2013.01); *A61F 2/74* (2021.08); *A61F 2002/503* (2013.01); *A61F 2002/5006* (2013.01); *A61F 2002/507* (2013.01);
(Continued)

(58) Field of Classification Search
CPC .. A61F 2/66; A61F 2/6607; A61F 2/70; A61F 2/74; A61F 2/60; A61F 2002/5006; A61F 2002/5007; A61F 2002/503; A61F 2002/5033; A61F 2002/5067; A61F 2002/507; A61F 2002/5073; A61F 2002/5086; A61F 2002/6642; A61F 2002/6657; A61F 2002/6664; A61F 2002/6692; A61F 2002/6818;
(Continued)

(56) References Cited

U.S. PATENT DOCUMENTS

2007/0050045 A1* 3/2007 Clausen .................... A61F 2/70
623/47
2009/0265019 A1* 10/2009 Christensen .............. A61F 2/66
623/55

(Continued)

*Primary Examiner* — Matthew J Lawson
*Assistant Examiner* — Aren Patel
(74) *Attorney, Agent, or Firm* — Maginot, Moore & Beck LLP

(57) ABSTRACT

A prosthetic foot has a frame, a forefoot keel, a heel keel, and an adjustable spring member. The frame couples to a prosthetic leg. The forefoot keel includes a first resilient substrate extending from the frame to the anterior end of the foot. The heel keel member includes a second resilient substrate extending from the frame to the posterior end. The first and second resilient substrates are load bearing substrates for a walking human. The adjustable spring member includes a third resilient substrate and a brake. The third resilient substrate has a first end directly or indirectly coupled to the brake, and a second end coupled to the forefoot keel proximate to the anterior end. The third resilient substrate extends through or around the first resilient member and the second resilient member. The brake provides resistance to the travel of the first end of the third resilient substrate in the superior direction.

17 Claims, 7 Drawing Sheets

Related U.S. Application Data

(60) Provisional application No. 62/601,104, filed on Mar. 9, 2017.

(51) Int. Cl.
  *A61F 2/50* (2006.01)
  *A61F 2/60* (2006.01)
  *A61F 2/68* (2006.01)
  *A61F 2/76* (2006.01)
  *A61F 2/74* (2006.01)

(52) U.S. Cl.
  CPC ............... *A61F 2002/5007* (2013.01); *A61F 2002/5033* (2013.01); *A61F 2002/5067* (2013.01); *A61F 2002/5073* (2013.01); *A61F 2002/5086* (2013.01); *A61F 2002/6642* (2013.01); *A61F 2002/6657* (2013.01); *A61F 2002/6664* (2013.01); *A61F 2002/6692* (2013.01); *A61F 2002/6818* (2013.01); *A61F 2002/701* (2013.01); *A61F 2002/704* (2013.01); *A61F 2002/7635* (2013.01)

(58) Field of Classification Search
  CPC .......... A61F 2002/701; A61F 2002/704; A61F 2002/7635
  See application file for complete search history.

(56) References Cited

U.S. PATENT DOCUMENTS

| | | | |
|---|---|---|---|
| 2012/0016493 A1* | 1/2012 | Hansen | A61F 2/6607 623/53 |
| 2014/0330393 A1* | 11/2014 | Ward | A61F 2/6607 623/24 |
| 2015/0328020 A1* | 11/2015 | Clausen | A61F 2/6607 623/25 |
| 2016/0310298 A1* | 10/2016 | Jonsson | A61F 2/66 |

* cited by examiner

FOOT PROSTHESIS WITH DYNAMIC VARIABLE KEEL RESISTANCE

This application is a continuation of U.S. patent application Ser. No. 15/916,520, filed Mar. 9, 2018, which in turn claims the benefit of U.S. Provisional Patent Application Ser. No. 62/601,104, filed Mar. 9, 2017, the entirety of each of which is incorporated herein by reference.

FIELD OF THE INVENTION

The present invention relates generally to foot and leg prosthesis systems, and more particularly, to foot prostheses used in such systems.

BACKGROUND

Foot and leg prosthetic systems enhance the mobility of people who have had all or part of a leg amputated. A foot prosthesis typically replaces the ankle joint and the foot, and may be connected below the knee of a patient when the leg has been amputated below the knee. However, foot prostheses can also be connected to an artificial knee when the leg has been amputated above the knee.

One common foot prosthesis is a passive, carbon fiber prosthetic foot. For example, the Agilix Prosthetic foot available from Freedom Innovations is an example of a carbon fiber foot that includes an upper carbon fiber substrate that extends from a toe portion to an ankle portion in a curved manner, and a lower carbon fiber substrate that extends from about the toe portion to a heel end. The shape and thickness of flexible carbon substrates provides spring action during the gait cycle, by deflecting and rebounding as they are progressively loaded and unloaded with the user's body weight. As the user moves through the gait cycle, the energy stored during early, middle and late stance is returned back to the user as the carbon springs are unloaded and allowed to dynamically return to their non-deflected positions.

The energy storage and release helps provide some of the support that is, in a non-amputated leg, provided by the muscles of the lower leg. However, the spring action of a carbon fiber foot has inherent limitations, and in fact does not approximate the elegant timing and torque changes of normal muscle action in in mid to late stance phase as the shin rotates about the foot. In normal human walking, there is a variable resistance to the saggital rotation of the shin relative to the foot driven by the muscles of the lower leg. The execution and efficiency of this variable resistance has implications on limb stability, gait efficiency, stride symmetry and the closed chain torques placed on proximal joints.

To better approximate the saggital timing and torque changes observed in normal lower limb muscles, various powered mechanisms have been implemented that provide a variable resistance during stance phase. These products often include motors, gears, and batteries, there by greatly increasing weight, cost and user inconvenience.

There is a need, therefore, for a system that provides variable keel resistance during stance phase that does not introduce drawbacks of the prior art system.

SUMMARY

At least some embodiments of the present invention address the above-described needs by providing a prosthetic foot that includes an adjustable spring mechanism that extends from the forefoot keel to a position posterior to the ankle area. The action of the adjustable spring mechanism provides a more anatomically accurate variable resistance of the shank over the foot as it moves into a dorsiflexed position in mid to late stance.

A first embodiment is a prosthetic foot having an anterior toe end, and a posterior heel end, a frame, a forefoot keel member, a heel keel member, and an adjustable spring member. The frame is configured to couple to a prosthetic leg. The forefoot keel member includes a first resilient substrate extending from the frame to the anterior toe end of the prosthetic foot. The first resilient substrate is configured as a load bearing substrate for a walking human. The heel keel member includes a second resilient substrate extending from the frame to the posterior heel end. The second resilient substrate is also configured as a load bearing substrate for a walking human. The adjustable spring member includes a third resilient substrate and a brake. The brake is configured to be coupled to the prosthetic leg. The third resilient substrate has a first end directly or indirectly coupled to the brake, and a second end coupled to the forefoot keel proximate to the anterior toe end. The third resilient substrate extends through or around the first resilient member and the second resilient member. The brake provides resistance to the travel of the first end of the third resilient substrate in the superior direction.

It will be appreciated that the above-described features and advantages, as well as others, will become more readily apparent to those of ordinary skill in the art by reference to the following detailed description and accompanying drawings.

DETAILED DESCRIPTION

Figure 1:
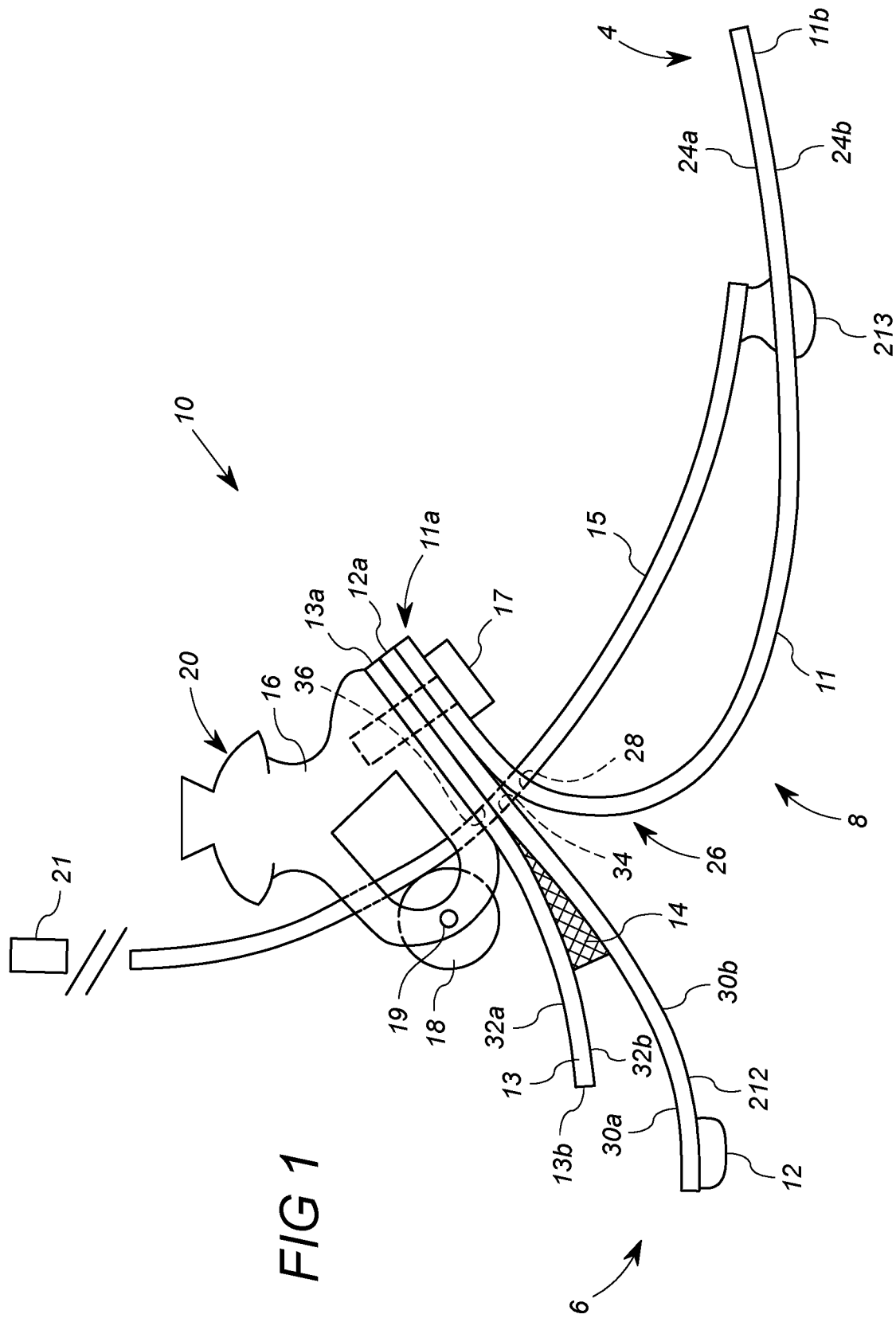
FIG. 1 shows a side plan representative drawing of a foot prosthesis according to at least one embodiment of the invention.

FIG. 1 shows a side plan view of a prosthetic foot 10 that incorporates principles of at least one embodiment of the invention. The prosthetic foot 10 is configured to attached to a prosthetic tibia, not shown in FIG. 1. The prosthetic tibia may take any suitable form. One example of a prosthetic tibia is discussed below in connection with FIGS. 2-4.

The prosthetic foot 10 has an anterior toe end 4, a posterior heel end 6, and an inferior sole region 8. The sole region 8 includes one or more surfaces that generally face the walking surface during the gait, and which engage the ground directly or through footwear. The prosthetic foot 10 includes an anchor frame 16, a forefoot keel 11, a heel keel 12, a rear keel buffer 13, an optional heel wedge 14, and an adjustable spring member that includes a drive spring 15 and a brake 21. In one embodiment, the prosthetic foot includes a heel force sensor 212 and a forefoot force sensor 213. In general, the anterior toe end 4 corresponds in relative position and gait function to anatomical human toes, the posterior heel end 6 corresponds in relative position and gait function to an anatomical human heel, and the sole region 8 corresponds in relative position and gait function to an anatomical human sole.

The anchor frame 16 is a rigid structural member than includes a top mount interface 20, an angled mount surface 22, a roller mount 19. In the anterior-posterior direction, the anchor frame 16 is disposed closer to the heel end 6. In the superior-inferior direction, the anchor frame 16 is disposed superior to (above the) sole region 8. The angled mount surface 22 generally faces downward and generally towards the anterior toe end 4. The top mount interface 20 is configured to be rigidly affixed to the inferior extent of a prosthetic tibia via any standard connection, not shown.

The forefoot keel 11 comprises a resilient substrate that has a proximal end 11a that is rigidly affixed to the anchor frame 16, and extends to a distal end 11b that is disposed at the anterior toe end 4 of the prosthetic foot 10. The forefoot keel member 11 is configured as a load bearing substrate, for example, constructed from carbon fiber, for a walking human. As a resilient substrate, the forefoot keel 11 further operates as a spring, compressing and storing energy as the forefoot keel 11 is pressed downward against the ground, and releasing energy as the forefoot keel 11 is lifted from the ground.

The forefoot keel 11 in this embodiment is a curved, elongate substrate having a first surface 24a and an opposite second surface 24b. The forefoot keel 11 is coupled to the anchor frame 16 via a fastener 17 such that a portion of the second surface 24b faces the angled mount surface 22. From the proximal end 11a, the resilient substrate of the forefoot keel member 11 extends downward adjacent to the angled mount surface 22 and posteriorly, away from the anterior toe end 4. The forefoot keel member 11 thereafter extends back anteriorly, toward the anterior toe end 4, such that at least a portion of the second surface 24b near the toe end 4 forms a bottom-most surface (and part of the sole region 8) of the prosthetic foot 10. The curvature of the forefoot keel 11 forms an inflection point 26 at which the substrate changes from extending rearward (posteriorly) and downward (inferiorly) to extending forward (anteriorly) and downward (inferiorly).

In this embodiment, the forefoot keel member 14 includes an opening 28 in the vicinity of, and in this embodiment, at or slightly proximally displaced from, the inflection point 26. The forefoot force sensor 213 is disposed on the second surface 24b near, but not at, the anterior toe end 4.

The heel keel 12 is also formed of a resilient substrate, and has a proximal end 12a and a distal end 12b. The proximal end 12a of the heel keel 12 is rigidly affixed to the anchor frame 16, via the fastener 17, adjacent to and congruent with the proximal end 11a of the forefoot keel 11. From the proximal end 12a, heel keel 12 extends in a curved manner toward the posterior heel end 6 of the prosthetic foot 10. The heel keel 12 is configured as a load bearing substrate, for example, constructed from carbon fiber, capable of bearing the load of a walking human. As a resilient substrate, the heel keel 12 further operates as a spring, compressing and storing energy as the heel keel 12 is pressed downward against the ground, and releasing energy as the heel keel 12 is lifted from the ground.

The heel keel 12 in this embodiment is a substantially rectangular substrate having a first surface 30a and an opposite, second surface 30b. The heel keel 12 is coupled to the angled mount surface 22 such that the first surface 30a faces the angled mount surface 22. The heel keel 12 extends downward (inferiorly) and backward (posteriorly) along the angled mount surface 22 toward the posterior heel end 6, and continues past the angled mount surface with a slight concave curve, in order to present a reduced angle from the horizontal plane nearer the heal end 6. As such, at least a portion of the second surface 30b near the heel end 6 forms a bottom-most surface (and part of the sole region 8) of the prosthetic foot 10. The heel force sensor 213 is affixed to the second surface 30b at the posterior heel end.

In this embodiment, the rear keel buffer 13 is another resilient substrate that extends posteriorly from the anchor frame 16. In particular, the rear keel buffer 13 includes a proximal end 13a and a distal end 13b, a first surface 32a, and a second surface 32b. The proximal end 13a rigidly affixed to the anchor frame 16 adjacent to and congruent to the proximal end 12a of the heel keel 12, such that the first surface 32a faces the angled mount surface 22.

The rear keel buffer 13 in this embodiment is a substantially rectangular substrate, and as discussed above, has a first surface 32a and an opposite, second surface 32b. From the distal end 13a, the rear keel buffer 13 extends downward and backward along the mount surface 22 toward the posterior heel end 6, and continues past the mount surface 22 with a slight concave curve. Apart from the proximal end 13a, which extends alongside (and abutting) the heel keel 12, the rear keel buffer 13 extends along but spaced apart from the first surface 30a of the heel keel 12. The optional wedge 14 is disposed between the first surface 30a of the heel keel 12 and the second surface 32b of the rear keel buffer 13. The rear keel buffer 13 and wedge 14 are configured as a spring, for example, to engage and absorb energy from the heel keel 12 after the heel keel 12 has been partially compressed during portion of the gait where the heel keel 12 is placed on the ground.

In this embodiment, each of the heel keel 12 and the rear keel buffer 13 includes a respective opening 34, 36 in the vicinity of, and just distal to (or below), the portion of the heel keel 12 and the rear keel buffer 13 that extend along the angled mount surface 22. It will be appreciated that the openings 28, 34 and 36 are shown in phantom in FIG. 1.

In this embodiment the drive spring 15 is a rigid or resilient substrate coupled between the brake 21 and the forefoot keel 11. The drive spring 15 may suitably be formed of carbon fiber, titanium, or other appropriate materials, and is preferably of a greater stiffness than the forefoot keel 11 and heel keel 12. The drive spring 15 is rigidly or pivotally attached to the upper surface 24a of the forefoot keel 11 near the anterior toe end 4, and is further coupled to the brake 21. To this end, the drive spring 15 passes through the openings 28, 32 and 34, in respectively, the forefoot keel 11, the heel keel 12, and the rear keel buffer 13, such that the drive spring 15 may move distally and proximally through the openings 26, 32, and 34. However, it will be appreciated that the drive spring 15 could alternatively pass around the forefoot keel 11, the heel keel 12, and the rear keel buffer 13 to allow such movement.

The drive spring 15 is curved, extending from a nearly vertical tangent proximate the brake 21 to a nearly horizontal tangent on the top surface 24a of the forefoot keel 11. The drive spring 15 engages the guide roller 18 during distal and proximal travel. The guide roller 18 is rotatably attached to an axle 19 mounted on the anchor frame 16, and is position to guide the travel of the drive spring 15 in the curved path.

The brake 21 is an arresting mechanism that is configured to provide resistance to the travel of the drive spring 15 in the superior and/or proximal direction. The brake 21 may suitably be a hydraulic cylinder, a mechanically adjustable or microprocessor-controlled hydraulic cylinder, motor, electromagnet, dynamic wedging mechanism, piezoelectric material, etc. Although the brake 21 as illustrated is disposed at the end of the drive spring 15, the brake 21 may be placed or inserted at any point along the drive spring 15 such that it is able to arrest (or increasingly resist) the motion of the drive spring 15 during late stance foot dorsiflexion. In the embodiment described herein, the brake 21 is operably coupled to receive signals from the sensors 212, 213, and includes at least some processing capability to adjust the braking force of the brake 21 in response to force measurement information within the received signals. The processor of the brake 21, not shown, may use the sensor signals to actively control the timing and deceleration of the drive spring 15. It will be appreciated the guide roller 18 may some embodiments incorporate structures or features that help arrest the travel of the drive spring 15 and thus forms part of the brake.

The operation of the prosthetic foot 10 is described with respect to the gait cycle. At initial contact, the heel keel 12 encounters a ground reaction force, which causes upward deflection of the heel keel 12. The upward deflection of the heel keel 12 can be cushioned and initially decelerated by the heel wedge 14, and is ultimately arrested with additional resistance from the rear keel buffer 13.

As the person's center of mass progresses over the prosthetic foot 10 into midstance, the energy stored within the heel keel 12 is released, contributing to the forward advancement and progression of the tibial component of the prosthesis, not shown in FIG. 1. If a heel force sensor 212 is utilized, then the processing device of the brake 21 uses the sensor data to help calculate load and timing of the mechanisms of the brake 21 to be employed later in the gait cycle, discussed below.

As the prosthetic foot 10 continues through midstance, the forefoot keel 11 begins to deflect proximally as it is loaded with weight and in response to the equal and opposite ground reaction force. Simultaneously, the drive spring 15 is effectively pushed through the openings 28, 34, 36, against the guide roller 18, and upwards superior to the anchor frame 16. The effective motion of the drive spring 15 is buffered by the guide roller 18. As the forefoot keel 11 deflects, the optional forefoot force sensor 213 provides measurement data that allows for assessment of walking force and the calculation of walking speed, force and timing. The information from the heel force sensor 212 may be used for the same purpose. The sensor information can be communicated to the processor of the brake 21, which can use the information to adjust the arresting force of the brake 21. However, in embodiments without the sensors 212, 213, the brake 21 may arrest or resist the movement of the drive keel 15 according to a preset, or manually adjustable value.

With the drive spring 15 movement arrested at the proper point of the gait, it can contribute to late-stance energy storage and release along with the foreforot keel 11, which has been storing energy as the foot began moving into mid-late stance dorsiflexion. The forefoot keel 11 and the arrested drive spring 15 will release their energy as weight is removed from the foot 10. During swing phase, the drive spring brake 21 will provide a controlled release of the drive spring 15 and allow it to return to its resting position in preparation for the next step.

The spring characteristics of the forefoot keel 11 and the heel keel 12 should be selected such that the prosthetic foot 10 is extremely compliant of the user at low walking speeds. As the speed and forces encountered during walking increase, the brake 21 will gradually increase the resistance on the drive spring 15 (either passively or actively), to create a fluid transition throughout the entire gait cycle.

Figure 2:
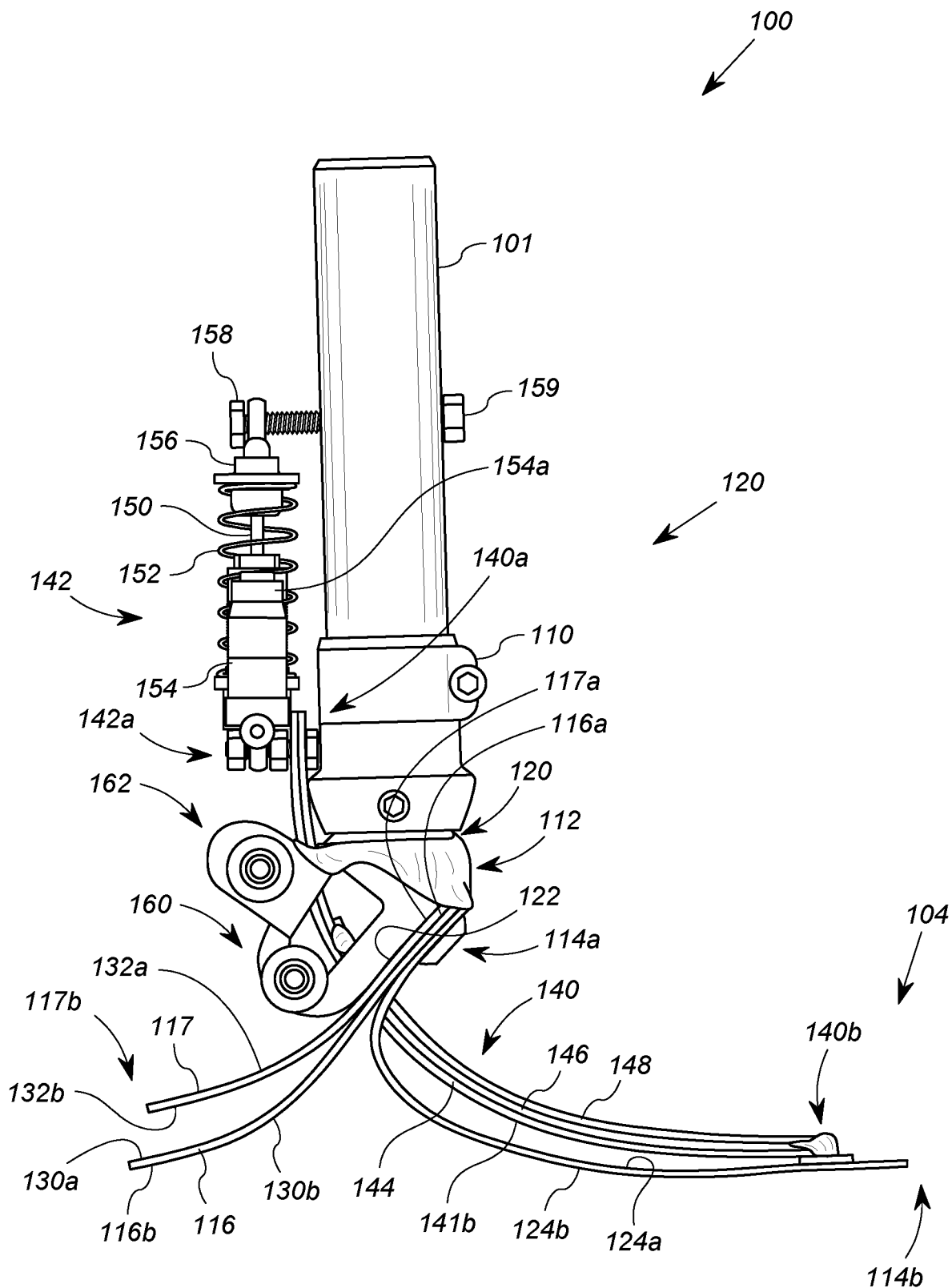
FIG. 2 shows a side plan representative drawing of an arrangement that includes a first embodiment of a foot prosthesis according to the invention.
Figure 3:
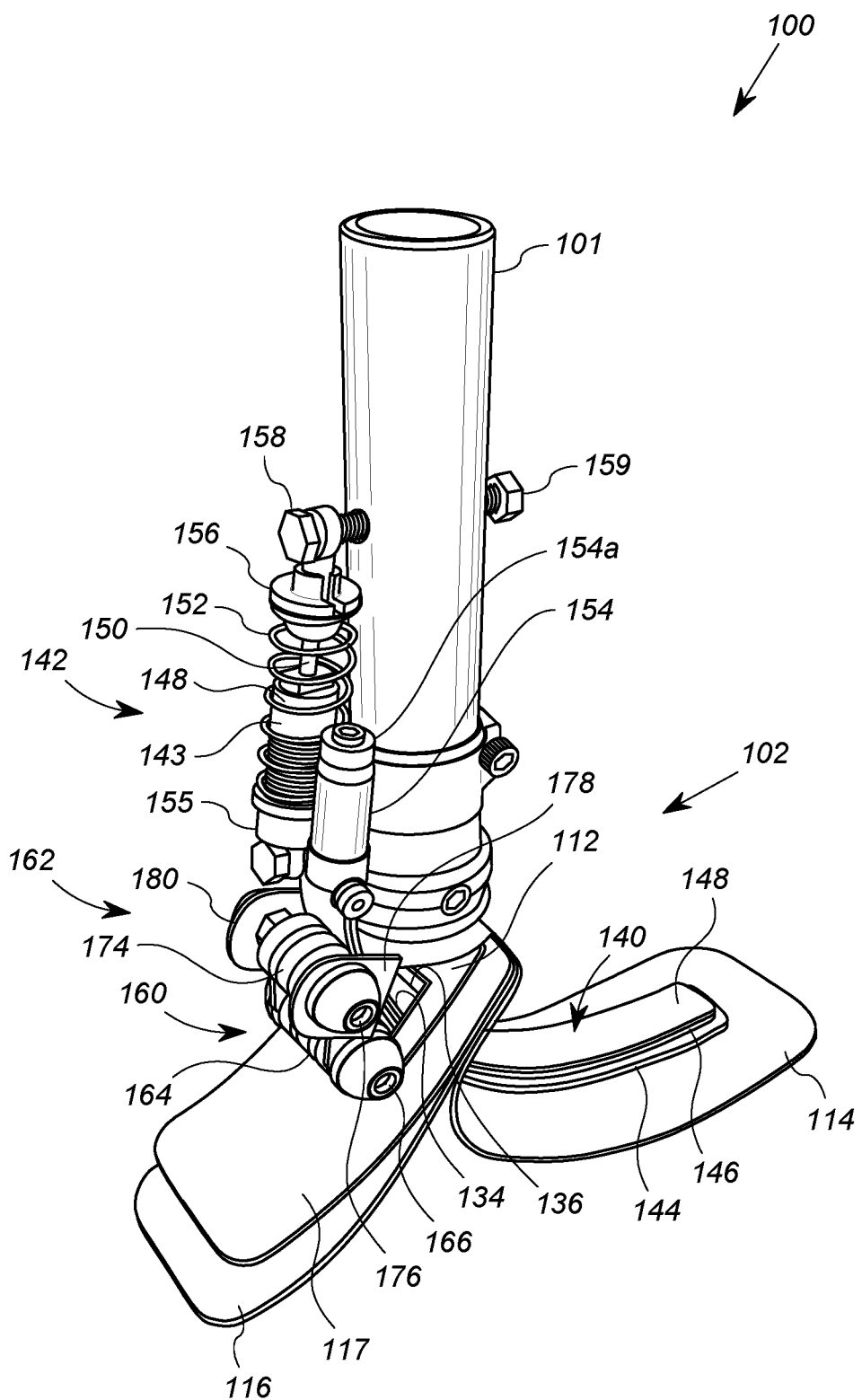
FIG. 3 shows a rear, elevated perspective view of the arrangement of FIG. 2.
Figure 4:
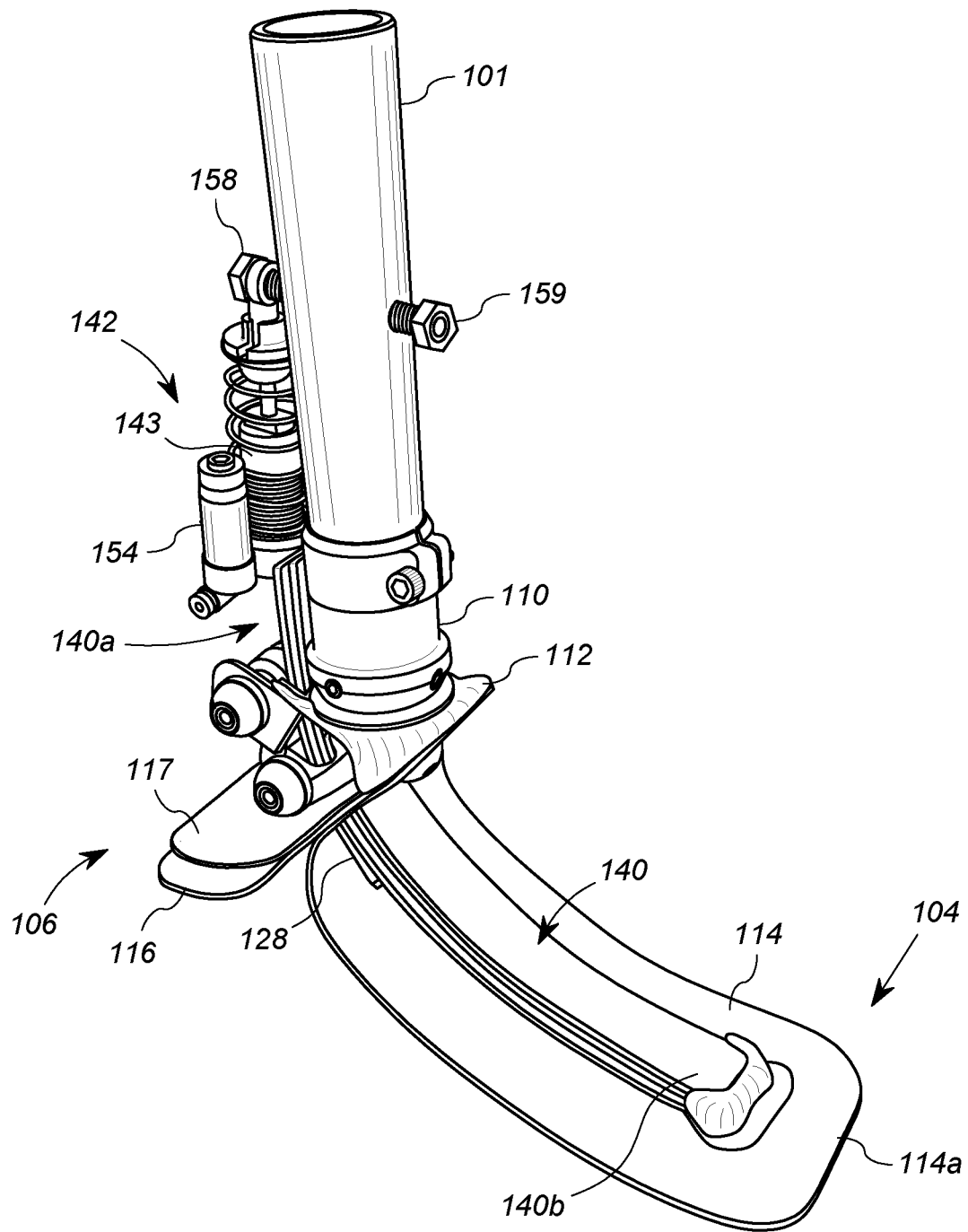
FIG. 4 shows a front, elevated perspective view of the arrangement of FIG. 2.

FIGS. 2 to 4 show in further detail a more detailed example of a foot prosthesis according to at least one embodiment described here. In particular, FIGS. 2 to 4 show different views of an arrangement 100 including a prosthetic foot 102 that incorporates principles of at least one embodiment of the invention. The arrangement 100 includes at least a portion of a prosthetic tibia 101 to which the prosthetic foot 102 may be attached. The upper portions of the prosthetic tibia 101, not shown, may take any form that attaches below the knee, or which attaches to a prosthetic knee or other prosthetic structures below the hip, also not shown.

The prosthetic foot 102 has an anterior toe end 104, a posterior heel end 106, and a sole region 108. The sole region 108 includes one or more surfaces that generally face the walking surface during the gait, and which engage the ground directly or through footwear. The prosthetic foot 102 includes a connector 110, an anchor frame 112, a forefoot keel member 114, a heel keel member 116, a rear keel buffer 117, and an adjustable spring member 118. In general, the anterior toe end 104 corresponds in relative position and gait function to anatomical human toes, the posterior heel end 106 corresponds in relative position and gait function to an anatomical human heel, and the sole region 108 corresponds in relative position and gait function to an anatomical human sole.

The anchor frame 112 is a rigid structural member than includes a top mount interface 120, an angled mount surface 122, and may otherwise include suitable support structures necessary to form a rigid structural frame. In the anterior-posterior direction, the anchor frame 112 is disposed closer to the heel end 106. In the superior-inferior direction, the anchor frame 112 is disposed superior to (above the) sole region 108. Thus the anchor frame 112 corresponds roughly in position to an anatomical ankle.

The angled mount surface 122 generally faces downward and towards the anterior toe end 104. The top mount interface 120 is rigidly affixed to the inferior extent of the prosthetic tibia 101 via the connector 110. The top mount plate 120 in this embodiment includes the connector 110. The connector 110 may be any standard connector configured to connect a prosthetic foot and ankle to a rigid prosthetic tibia. In this embodiment, the prosthetic tibia 101 is an elongate, rigid and human weight bearing structure. As shown in FIGS. 2 to 4, at least one embodiment of the prosthetic tibia 101 is formed from a [steel/aluminum/titanium?] tube.

The forefoot keel member 114 comprises a resilient substrate that has a proximal end 114a that is rigidly affixed to the anchor frame 112, and extends to a distal end 114b that is disposed at the anterior toe end 104 of the prosthetic foot 102. The forefoot keel member 114 is configured as a load bearing substrate, for example, constructed from carbon fiber, for a walking human. As a resilient substrate, the forefoot keel member 114 further operates as a spring, compressing and storing energy as the forefoot keel 114 is pressed downward against the ground, and releasing energy as the forefoot keel 114 is lifted from the ground.

The forefoot keel member 114 in this embodiment has a curved, elongate shape, and has a first surface 124a and an opposite second surface 124b. The forefoot keel member 114 is coupled to the anchor frame 112, such that a portion of the second surface 124b faces the angled mount surface 122. From the proximal end 114a, the resilient substrate of the forefoot keel member 114 extends downward adjacent to the angled mount surface 122 and posteriorly away from the anterior toe end 104. The forefoot keel member 114 thereafter extends back anteriorly toward the anterior toe end 104, such that at least a portion of the second surface 124b near the toe end 104 forms a bottom-most surface (and part of the sole region 108) of the prosthetic foot 102. The curvature of the forefoot keel member 114 forms an inflection point 126 at which the member 114 transitions from extending rearward (posteriorly) and downward (inferiorly) to extending forward (anteriorly) and downward (inferiorly).

In this embodiment, the forefoot keel member 114 includes an opening 128 in the vicinity of, and in this embodiment, at or slightly proximally displaced from, the inflection point 126. (See FIG. 4). The opening 128 is designed to have a width that allows the surrounding portions of the substrate of the member 114 to maintain its ability to bear human weight without compromising structural integrity. For example, the width of the opening may suitably be less than 50% of the width of the substrate 124.

The heel keel member 116 is also formed of a resilient substrate, and has a proximal end 116a and a distal end 116b. The proximal end 116a of the heel keel member 116 is rigidly affixed to the anchor frame 112 adjacent to and congruent to the proximal end 114a of the forefoot keel 114. From the proximal end 116a, heel keel member 116 extends in a curved manner toward the posterior heel end 106 of the prosthetic foot 102. The heel keel member 116 is configured as a load bearing substrate, for example, constructed from carbon fiber, capable of bearing the load of a walking human. As a resilient substrate, the heel keel 116 further operates as a spring, compressing and storing energy as the heel keel 116 is pressed downward against the ground, and releasing energy as the heel keel 116 is lifted from the ground.

The heel keel member 116 in this embodiment has a substantially rectangular shape and includes a first surface 130a and an opposite, second surface 130b. The heel keel member 116 is coupled to the angled mount surface 122 such that the first surface 130a faces the angled mount surface 122a. The heel keel member 116 extends downward and backward along the mount plate 122 toward the posterior heel end 106, and continues past the angled mount plate 122 with a slight concave curve, in order to present reduced angle from the horizontal nearer the heal end 106. As such, at least a portion of the second surface 130b near the heel end 106 forms a bottom-most surface (and part of the sole region 108) of the prosthetic foot 102.

In this embodiment, the rear keel buffer 117 is another resilient substrate that extends posteriorly from the anchor frame 112. In particular, the rear keel buffer 117 includes a proximal end 117a and a distal end 117b, a first surface 132a, and a second surface 132b. The proximal end 117a rigidly affixed to the anchor frame 112 adjacent to and congruent to the proximal end 116a of the heel keel 116, such that the first surface 132a faces the angled mount surface 122.

The rear keel buffer 117 in this embodiment has a substantially rectangular shape, and includes a first surface 132a and an opposite, second surface 132b. From the distal end 117a, the rear keel buffer 117 extends downward and backward along the mount plate 122, and past the mount plate 122, toward the posterior heel end 106 with a slight concave curve, in order to present reduced angle from the horizontal nearer the heal end 106. Apart from the proximal end 117a, which extends alongside (and abutting) the heel keel 116, the rear keel buffer 117 extends along but space apart from the first surface 130a of the heel keel member 116. The rear keel buffer 117 is configured as a spring, for example, and is configured to engage and absorb energy from the heel keel member 116 after the heel keel 116 member 116 has been partially compressed during portion of the gait where the heel keel 116 is placed on the ground.

It will be appreciated that in this embodiment, the forefoot keel member 114, the heel keel member 116, and the rear keel buffer 117 are coupled in a stacked manner to the anchor frame 112. The first surface 117a of the rear keel buffer 117 couples directly to the angled mount surface 122, the first surface 116a of the heel keel member 116 abuts the second surface 117b of the rear keel buffer 117, and the second surface 114b of the forefoot keel member 114 abuts the second surface 116b of the heel keel member 116.

It will be appreciated that the forefoot keel member 114, the heel keel member 116, and the rear keel buffer 117 need not be formed as separate elements, but instead may be integrally formed, as they all emanate from the same distal structure at the anchor frame 112. Indeed, in some embodiments, the anchor frame 112 and one or more of the members 114, 116, and 117 can be formed as an integral unit.

In this embodiment, each of the heel keel member 116 and the rear keel buffer 117 includes a respective opening 134, 136 in the substrate 124 in the vicinity of, and in this just distal to (or below), the portions of the members 116, 117 that extend along the angled mount surface 122. The opening 134 is designed to have a width that allows the heel keel member 116 to maintain its ability to bear human weight without compromising structural integrity. For example, the width of the opening may suitably be less than 50% of the width of the substrate of the heel keel member 116. The opening 136 likewise as a width that does not otherwise interfere with the spring function of the rear keel buffer.

The adjustable spring member 118 in the embodiment described herein includes at least one resilient substrate forming a drive spring 140 and a brake 142. The brake 142 is configured to be coupled to the prosthetic tibia 101 above the anchor frame 112. The drive spring 140 is a resilient substrate having a first end 140a coupled to the brake 142 at a position posterior to and above the anchor frame 112, and a second end 140b coupled to the forefoot keel 114 proximate to the anterior toe end 104.

The drive spring 140 is an exemplary embodiment of the drive spring 15 of the embodiment of FIG. 1, and has a similar function. In this embodiment, the drive spring 140 includes multiple layers 144, 146, 148 of substrate material, each layer 144, 146 and 148 having substantially the same in thickness and physical properties as the heel keel member 116 and the forefoot keel member 114. The multilayered substrate 140 therefore has an increased overall stiffness than the keel members 114, 116.

In this embodiment, only the layers 144, 146 extend substantially from the first end 140a to the second end 140b. The layer 148 extends from the first end 140a to an intermediate position adjacent the anchor frame 112, just proximally to the openings 128, 134, and 136. This partial resilient layer 148 assists in the bending characteristic of the substrate 140 by providing additional stiffness to the distal half of the substrate 140. It will be appreciated that the differences in stiffness may be carried out in other ways, such as by using a single substrate with varying thickness, and/or different materials. The second end 140b of the drive spring 140 is fixedly secured to the first side 124a of the forefoot keel member 114, and the first end 140a is coupled to a first end 142a of the brake 142. The multilayered substrate 140 is curved, extending from a nearly vertical tangent at the first end 140a to a nearly horizontal tangent at the second end 140b. The multilayered substrate 140 extends through the openings 128, 134 and 136, and thus has a width that is less than the width of those openings. Thus, the drive spring 140 of the adjustable brake 118 extends through each of the forefoot keel member 114, the heel keel member 116, and the rear keel buffer 117 from anterior toe end 104 to the position posterior to the prosthetic tibia 101 and superior to at least the angled mount surface 122 of the anchor frame 112.

The brake 142 is a structure or group of structures that are configured to provide resistance to the travel of the first end 140a of the resilient substrate in the superior direction. In this embodiment, the brake 142 is a vertically disposed hydraulic cylinder 143 and a return spring 152. The hydraulic cylinder 143 in this embodiment includes a barrel 148, a piston rod 150, a hydraulic control 154 and first and second end caps 155, 156. The barrel 148 contains the hydraulic mechanisms, such as the piston and associate seals, not shown, but which would be known in the art. The piston rod 150 extends into and out of the barrel 148 in the longitudinal directional, and travels longitudinally into and out of the barrel as a function of, among other things, the operation of the hydraulic cylinder 143.

The first end cap 155 is coupled to the barrel 148 and includes a boss or loop to facilitate connection of the first end cap 155 to the first end 140a of the drive spring 140. The second end cap 156 is fixedly coupled to the end of the piston rod 150, and includes a boss or loop to facilitate connection via bolt 158 and nut 159 to the prosthetic tibia 101 at a fixed vertical location. It will be appreciated that the exact connection mechanisms between the end cap 155 and the drive spring 140, and between the end cap 156 and the prosthetic tibia 101, may take any suitable form.

The return spring 152 is disposed about the barrel 148 and piston rod 150, and extends between the end caps 155, 156. Accordingly, the longitudinal travel of the piston rod 150 increases or decreases the distance between the end caps 155, 156. Moreover, because the second end cap 156 is in a fixed vertical position with respect to the prosthetic tibia 101, the first end cap 155 moves vertically with any travel of the piston rod 150. In general, the return spring 152 and the hydraulic resistance of the hydraulic cylinder 143 resist compression or inward travel of the piston rod 150. The hydraulic control 154 allows for adjustment of the force necessary to push the piston rod 150 into the barrel 148. To this end, a rotatable adjustment element 154a can be used to increase or decrease the hydraulic resistance of the hydraulic cylinder 143.

It can therefore be seen that the brake 142, and in particular, the return spring 152 and the hydraulic cylinder 143 resist motion of the second end 140b of the resilient substrate in the superior direction.

In the embodiment of FIGS. 1-3, the anchor frame 112 also includes first and second guide members 160, 162. The guide member 160 includes a roller 164 disposed on an axle 166 rotatably supported by suitable features of the anchor frame 112. The guide member 160 engages the second side 141b of the drive spring 140 to help direct the travel of the second end 140b of the drive spring 140 in the vertical direction responsive to upward force on the first end 140a that results from dorsiflexion, as will be discussed below. The guide member 162 likewise includes a roller 174 disposed on an axle 176 rotatably supported between to posts 178, 180. The guide member 162 also engages the second side 141b of the drive spring 140 to help direct the travel of the second end 140b of the drive spring 140 in the vertical direction responsive to upward force on the first end 140a that results from dorsiflexion.

The operation of the prosthetic foot 102 is described with respect to the gait cycle. At initial contact, the heel keel member 116 encounters a ground reaction force, which causes upward deflection of the heel keel 116. The upward deflection of the heel keel 116 can travel until it engages the rear keel buffer 117. The rear keel buffer 117 thereafter cushions and decelerates the deflection of the heel keel member 116.

As the person's center of mass progresses over the prosthetic foot 102 into midstance, the energy stored within the heel keel member 116 is released, contributing to the forward advancement and progression of the prosthetic tibia 101. As the prosthetic foot 102 continues through midstance, the forefoot keel member 114 begins to deflect proximally as it is loaded with weight and in response to the equal and opposite ground reaction force. Simultaneously, the drive spring 140 is effectively pushed through the openings 128, 134, 136, against the guide rollers 164, 174, and upwards superior to the anchor frame 112. The effective motion of the drive spring 140 is buffered by the guide rollers 164, 174. The first end 140a moves upward, thereby forcing the first end cap 155 of the brake 142 towards the second end cap 156. Because the second end cap 156 is anchored in a vertical location, the movement of the first end 140a and the first end cap 155 compresses the return spring 152 and forces the piston rod 150 into the barrel 148. Thus, the amount of resistance to travel is a function of vertical position, the spring elasticity, and the hydraulic cylinder force setting of the hydraulic control 154.

The hydraulic cylinder force setting may be manual, in which case the hydraulic force may be left in a default walking setting, which is based on the user's weight and other conventional factors. In such a case, if the user decides to participate in an activity with greater impact, such as running, or hiking with extra weight, the user can manually adjust the hydraulic control 154 (e.g., rotating the adjustment element 154) to greater resistance. The user can then change the setting back to the default walking setting when the activity is completed. In other embodiments, the hydraulic control 154 may include or be connected to a processing circuit that cooperates with a motor or other means automatically adjusts the resistance based on data indicative of activity, such as force measurements from sensors such as the sensors 212 and/or 213 of FIG. 1. In any event, the increased resistance provided through the adjustable spring member 118 reduces force on the knee, not shown, and provides a more natural gait.

Referring again to the operation of the arrangement 100 of FIGS. 2 to 4, after the movement of the drive spring 140 has been arrested at the proper point of the gait, it can contribute to late-stance energy storage and release along with the forefoot keel member 114, which has been storing energy as the foot began moving into mid-late stance dorsiflexion. The energy stored in the return spring 152 and drive spring 140 will release their energy as weight is removed from the foot 102.

As with the embodiment of FIG. 1, the spring characteristics of the forefoot keel member 114 and the heel keel 116 should be selected such that the prosthetic foot 102 is extremely compliant of the user at low walking speeds. As the speed and forces encountered during walking increase, the brake 142 will gradually increase the resistance on the drive spring 140 (either passively or actively), to create a fluid transition throughout the entire gait cycle.

As discussed above in connection with FIG. 1, the brake 21 may take many forms and/or include other mechanism. FIGS. 2 to 4 show an exemplary embodiment in which the brake 142 includes a hydraulic cylinder 143. However, in another embodiment, the roller 18 of FIG. 1 or the rollers 164, 174 of FIGS. 2 to 4 may be replaced by a cam.

Figure 5:
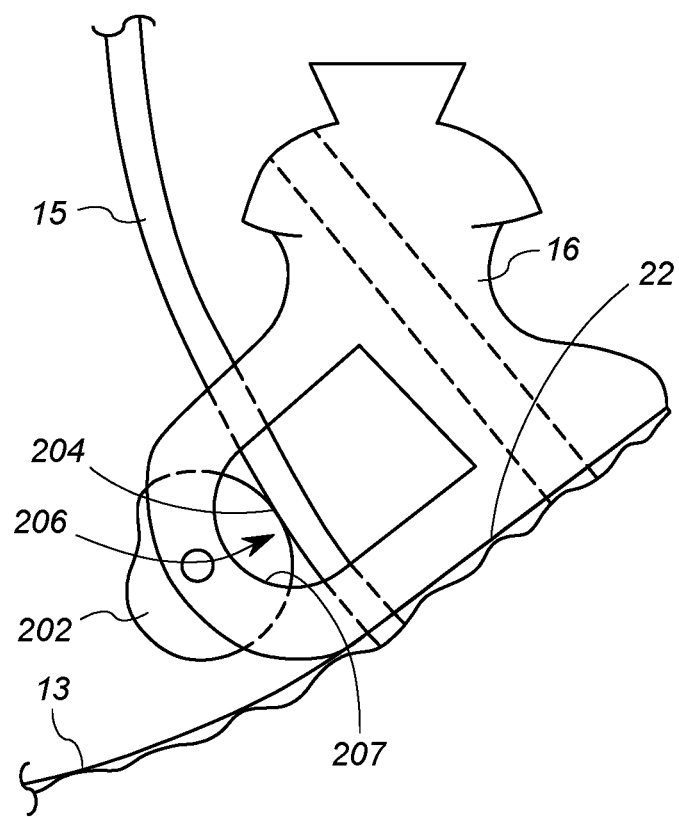
FIG. 5 shows a side plan, fragmentary view of a portion of an alternative embodiment prosthetic foot of FIG. 1.

For example, FIG. 5 shows a side plan, fragmentary view of a portion of an alternative embodiment prosthetic foot 10 of FIG. 1, wherein a cam 202 has replaced the roller 18 on the roller mount 19 of FIG. 1. The cam 202 has a roller surface 204 that engages the drive spring 15 of FIG. 1, and rotates about an axis 206. The radial distance 207 from the axis 206 to the roller surface 204 varies, increasing in the clockwise direction in this embodiment. The increasing radius of the roller surface 204 thereby provides a camming action, and increase resistance, as the drive spring 15 moves in the proximal/superior direction. The cam 202 may constitute all or part of a braking mechanism 21 providing the operation described above in connection with FIG. 1. It will be appreciated that the cam 202 may readily be used in the embodiment of FIGS. 2 to 4 as well.

Figure 6:
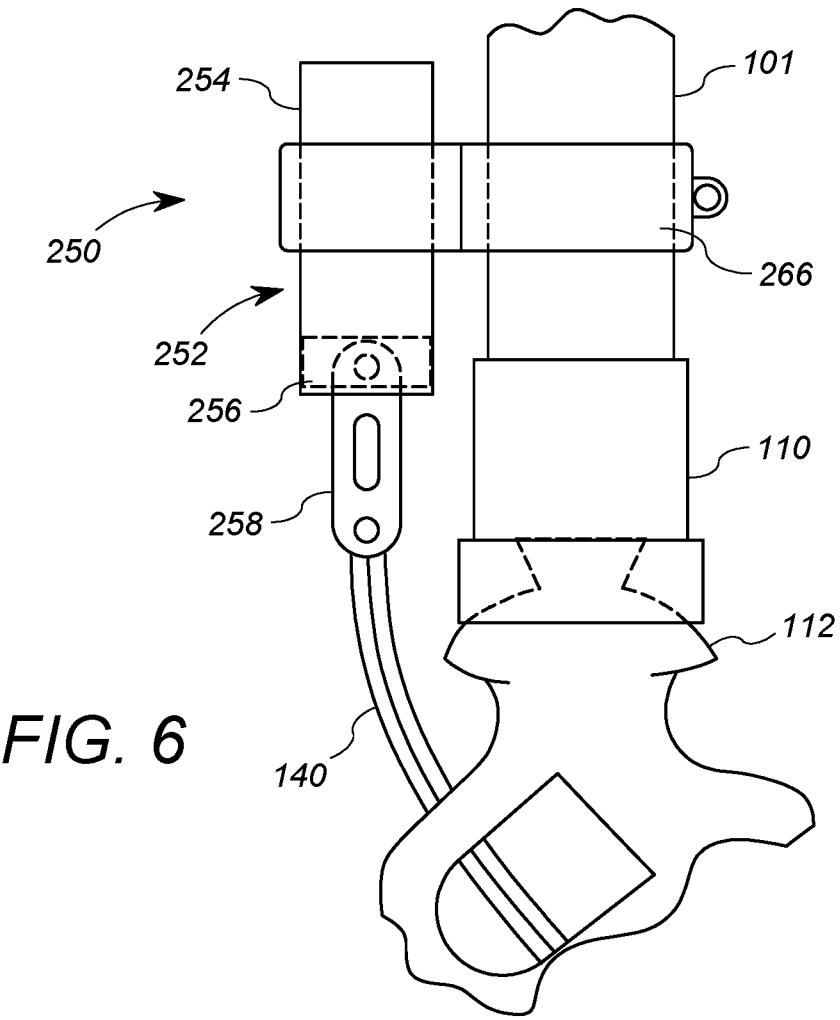
FIG. 6 shows a fragementary side plan view of a part of the prosthetic foot of FIG. 2 with an alternative braking mechanism 250.
Figure 7:
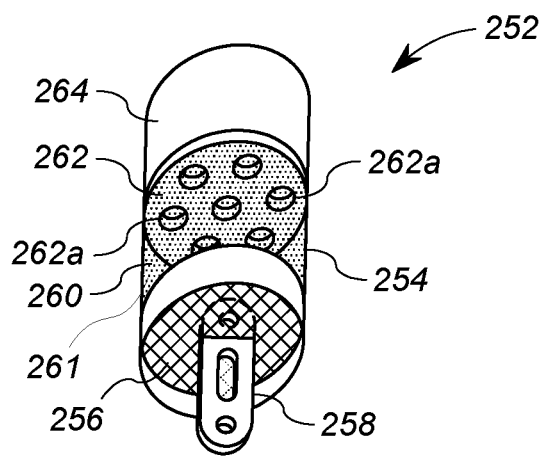
FIG. 7 shows a cutaway perspective view of an exemplary embodiment of a fluid cylinder of the braking mechanism of FIG. 6.

FIGS. 6 and 7 show yet another braking mechanism 250 that may be used in the embodiments of FIGS. 1 to 4. FIG. 6 shows a fragementary side plan view of a part of the prosthetic foot 102 of FIG. 2 with the braking mechanism 250 replacing the hydraulic cylinder 243 as the brake 242. The braking mechanism 250 includes a non-Newtonian fluid cylinder 252.

FIG. 7 shows a cutaway perspective view of an exemplary embodiment of the fluid cylinder 252. The fluid cylinder includes a barrel 254, a plunger 256, a pivot link 258, a first reservoir 260 containing a non-Newtonian fluid 261, such as a dilatant fluid, a strainer 262, and a second reservoir 264 that includes air. The plunger 256 is operably coupled to move axially within the barrel 254. The strainer 262 is mounted within the barrel 254 such that it separates the first reservoir 260 from the second reservoir 264. The strainer 262 includes apertures 262a that allow fluid communication between the first reservoir 260 and the second reservoir 264.

Referring again to FIG. 6, the barrel 254 is coupled to the prosthetic tibia 101 via a cylinder clamp 266, and the pivot link 258 is pivotally coupled to the drive spring 140.

When the drive spring 140 is displaced during the gait cycle, the plunger 256 displaces in the superior direction, into the first reservoir 260. The non-Newtonian fluid 261 within the first reservoir 260 is then pushed through the apertures 262a of the strainer 262. The movement of the non-Newtonian fluid through the apertures 262a is a function of the size of the apertures 262a and the force placed on it by the plunger 256. The fluid 261 enters the second reservoir 264 which has a predetermined level of air compression. As the load is removed from the drive spring 140 through the swing phase of the gait, the pressurized air in the second reservoir acts as a spring to push fluid 261 back into the first reservoir 260. The brake 250 is thus ready for the next gait cycle.

Thus, in the embodiment described above, the non-Newtonian fluid 261 inherently provides the braking resistance to the drive spring 140 that is proportional to the load placed on it. As such, the need for a processor (and its battery power) to adjust resistance based on force is eliminated. The need for the sensors 212 and 213 shown in FIG. 1 may also be eliminated.

It will be appreciated that the prosthetic foot embodiments described herein are sized and configured to be used with an industry standard footshell, not shown, but which would be known in the art. It will further be appreciated that embodiments of the prosthetic foot described herein that include processing units can include a myoelectrode plug/adaptable which allows commercially available myoelectrodes to be integrated into a prosthetic socket. In the embodiment described herein, the various adjustments to stiffness (e.g. adjusting the hydraulic cylinder 243 resistance) can be user controlled via the microprocessor interpretation.

Figure 8:
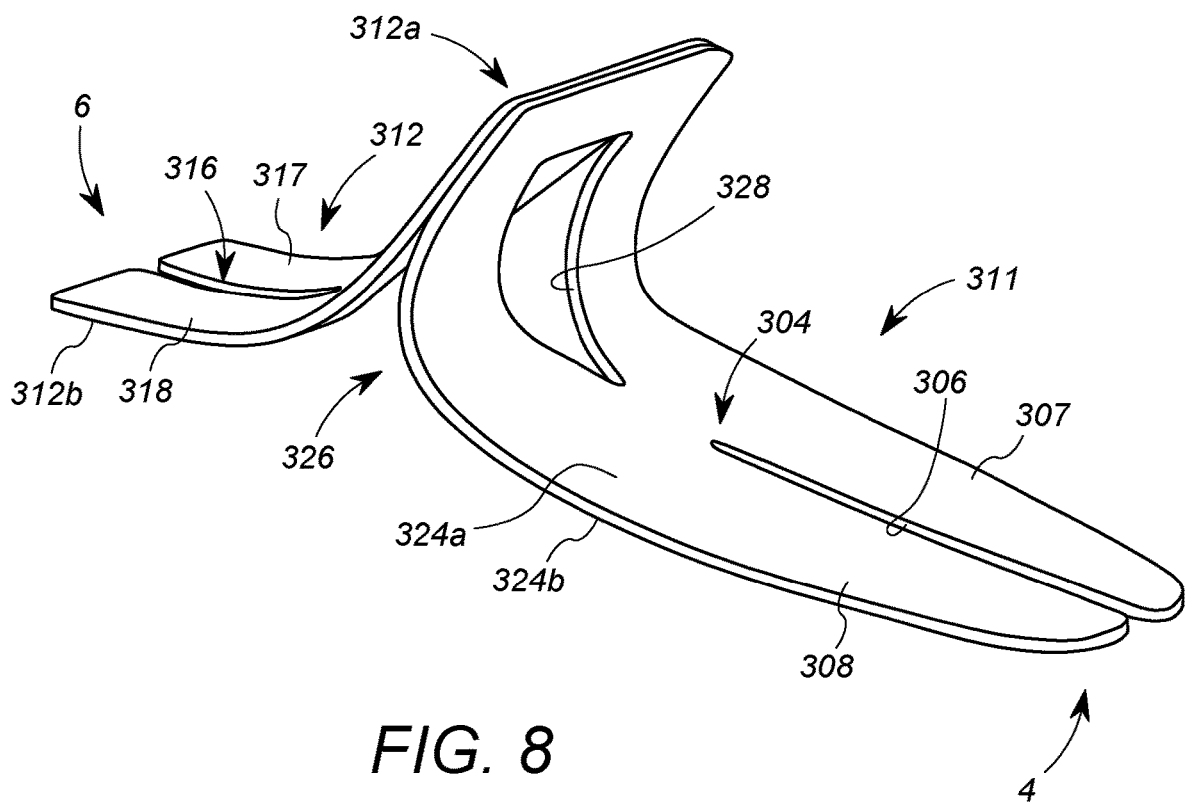
FIG. 8 shows the a perspective view of an alternative embodiment of a forefoot keel and heel keel that may be used in the prosthetic foot FIG. 1.
Figure 9:
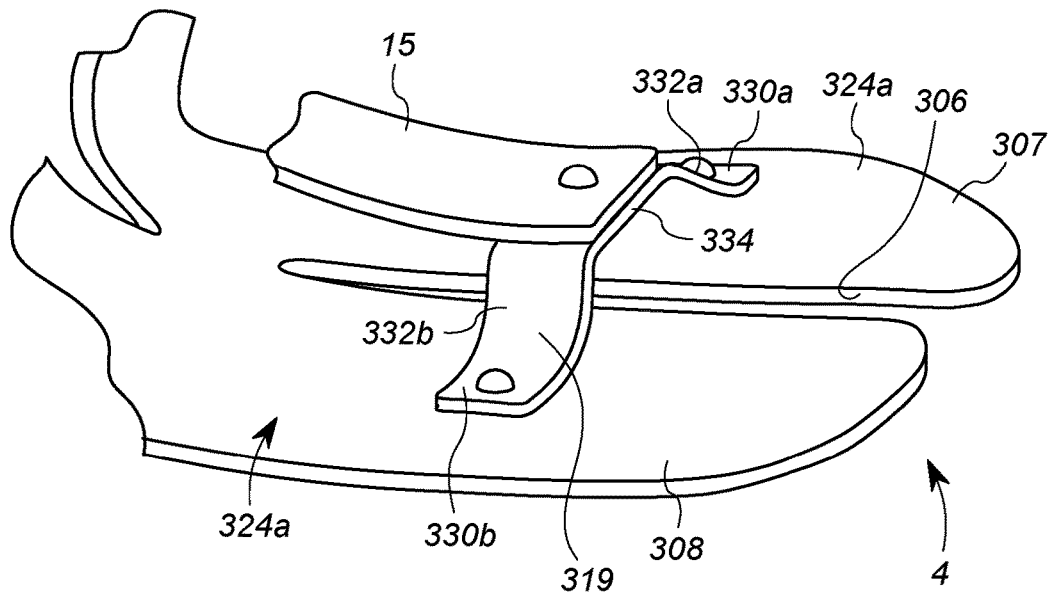
FIG. 9 shows a fragmentary perspective view of the forefoot keel of FIG. 8 with the drive spring apart from the rest of the prosthetic foot of FIG. 1.

FIGS. 8 and 9 illustrate an alternative embodiment of a forefoot keel 311 and heel keel 312 that may be used in place of the forefoot keel 11 and heel keel of FIG. 1. FIG. 8 shows the a perspective view of the forefoot keel 311 and heel keel 312 apart from the rest of the prosthetic foot 10 of FIG. 1. FIG. 9 shows a fragmentary perspective view of the forefoot keel 311 with the drive spring 15 apart from the rest of the prosthetic foot 10 of FIG. 1. It will be appreciated that the remaining structures of the prosthetic foot not shown in FIGS. 8 and 9 may take the form of the corresponding structures in any of FIGS. 1 through 7.

The forefoot keel 311 in this embodiment is a curved, elongate substrate that is split from the anterior toe end 4 to an intermediate position 304 of the substrate. The split 306 is a void between first and second fingers or extensions 307, 308 that extend to the anterior toe end 4. The split 306 allows for independent flexing of the fingers 307, 308. As a result, the split 306 can allow for more effective inversion, pronation and supination. Like the forefoot keel 11, the forefoot keel 311 has a first surface 324a, an opposite second surface 324b and an opening 328 through which the drive spring 15, not shown in FIG. 8, passes. The forefoot keel 311 is coupled to and extends along the anchor frame, not shown in FIG. 8, in the same manner as described above.

As with the embodiments of FIGS. 1 to 4, the curvature of the forefoot keel 311 forms an inflection point 326 at which the substrate changes from extending rearward (posteriorly) and downward (inferiorly) to extending forward (anteriorly) and downward (inferiorly). The position 304 at which the split 306 terminates is between the anterior toe end 4 and the inflection point 326. In this embodiment, the split 306 terminates between the anterior toe end 4 and the opening 328.

The heel keel 312 is also formed of a split, resilient substrate, and has a proximal end 312a and a distal end 312b. The proximal end 312a of the heel keel 312 is rigidly affixed to, and extends from, the anchor frame, not shown in FIG. 8, in the same manner as discussed above in connection with FIGS. 1-4. The split 316 defines a space between first and second fingers or extensions 317, 318 that extend to the posterior heel end 6. The split 316 extends from the distal end 312b (at the posterior heel end 6) to a position intermediate of the proximal end 312a and the distal end 312b.

FIG. 9 shows an exemplary mount 319 for use in mounting the drive spring 15 to the fingers 307, 308 of the split forefoot keel 311. The mount 319 is a preferably rigidly flexible structure, and may be formed of fiberglass or carbon fiber, by way of example. The mount 319 connects the distal end of the drive spring 15 to each of the fingers 307, 308. In this case, the mount 319 includes a substrate having mounting portions 330a, 330b, inclined portions 332a, 332b, and a drive spring mount 334. The mounting portions 330a, 330b are disposed on the first surface 324a of the respective fingers 307, 308. The drive spring mount 334 is a curved or straight portion of the substrate to which the drive spring 15 is directly attached. The inclined portions 332a, 332b, extend from the respective mounting portions 330a, 330b in an inclined manner to the drive spring mount 334. Such a structure allows for the benefit of split toe and split heel keels while retaining at least some of the benefits of the drive springs described herein. It will be appreciated that the mount 318 may take other forms that allow for moderately independent movement of the fingers 307, 308 while still effectively translating force through the drive spring 15.

The above-described embodiments are merely exemplary, and those of ordinary skill in the art may readily devise their own implementations and modifications that incorporate the principles of the present invention and fall within the spirit and scope thereof.

What is claimed is:

1. A prosthetic foot having an anterior toe end, and a posterior heel end, comprising:
    a frame configured to couple to a prosthetic leg, the frame including a top mount interface configured to be rigidly affixed to the inferior extent of a prosthetic tibia,
    a forefoot keel member including a first resilient substrate extending from the frame to the anterior toe end of the prosthetic foot, the first resilient substrate configured as a load bearing substrate for a walking human;
    a heel keel member including a second resilient substrate extending from the frame to the posterior heel end, the second resilient substrate configured as a load bearing substrate for a walking human;
    a brake configured to resist a force in a vertical direction from inferior to superior with respect to the prosthetic leg;
    a third resilient substrate having a first end and a second end, the first end extending vertically proximate to the brake vertically past a vertical level of a top-most part of the top mount interface and coupled to the brake, the second end of the third resilient substrate coupled to the forefoot keel proximate to the anterior toe end;
    a guide configured to direct the travel of the first end of the third resilient member in the vertical direction responsive to force on the second end that results from dorsiflexion.

2. The prosthetic foot of claim 1, wherein the brake is configured to allow at least some movement of the first end of the third resilient member while resisting movement of the first end of the third resilient member.

3. The prosthetic foot of claim 2, wherein the brake includes a vertically mounted spring operably coupled to the first end of the third resilient member.

4. The prosthetic foot of claim 3, wherein the brake includes a spring disposed about the hydraulic cylinder, and wherein the spring and the hydraulic cylinder resist motion of the first end of the third resilient substrate in the superior direction.

5. The prosthetic foot of claim 2, wherein the brake comprises a vertically mounted hydraulic cylinder.

6. The prosthetic foot of claim 5, wherein the hydraulic cylinder has an adjustable resistance.

7. The prosthetic foot of claim 1 wherein the guide includes at least one roller operably rotatably mounted to the frame, the at least one roller including the surface.

8. The prosthetic foot of claim 7, wherein the guide member includes a cam operably rotatably mounted to the frame.

9. The prosthetic foot of claim 1, wherein the guide is mounted to the frame.

10. A prosthetic foot having an anterior toe end, and a posterior heel end, comprising:
    a frame configured to couple to a prosthetic leg,
    a forefoot keel member including a first resilient substrate extending from the frame to the anterior toe end of the prosthetic foot, the first resilient substrate configured as a load bearing substrate for a walking human;
    a heel keel member including a second resilient substrate extending from the frame to the posterior heel end, the second resilient substrate configured as a load bearing substrate for a walking human;
    a brake configured to resist a force in a vertical direction from inferior to superior with respect to the prosthetic leg;
    a third resilient substrate having a first end and a second end, the first end extending vertically proximate to the brake and coupled to the brake, the second end of the third resilient substrate coupled to the forefoot keel proximate to the anterior toe end;
    a guide configured to direct the travel of the first end of the third resilient member in the vertical direction responsive to force on the second end that results from dorsiflexion,
    wherein the second end of the third resilient substrate is disposed above a top surface of the first resilient substrate of the forefoot keel member proximate to the anterior toe end.

11. The prosthetic foot of claim 10, wherein the brake is configured to allow at least some movement of the first end of the third resilient member while resisting movement of the first end of the third resilient member.

12. The prosthetic foot of claim 11, wherein the brake includes a vertically mounted spring operably coupled to the first end of the third resilient member.

13. The prosthetic foot of claim 12, wherein the brake includes a spring disposed about the hydraulic cylinder, and wherein the spring and the hydraulic cylinder resist motion of the first end of the third resilient substrate in the superior direction.

14. The prosthetic foot of claim 11, wherein the brake comprises a vertically mounted hydraulic cylinder.

15. The prosthetic foot of claim 14, wherein the hydraulic cylinder has an adjustable resistance.

16. The prosthetic foot of claim 10 wherein the guide includes at least one roller operably rotatably mounted to the frame, the at least one roller including the surface.

17. The prosthetic foot of claim 16, wherein the guide member includes a cam operably rotatably mounted to the frame.

* * * * *